United States Patent [19]

Iwane et al.

[11] Patent Number: 5,442,103
[45] Date of Patent: Aug. 15, 1995

[54] PROCESS FOR PRODUCING 2,6-NAPHTHALENEDICARBOXYLIC ACID

[75] Inventors: Hiroshi Iwane; Takahiro Sugawara; Katsufumi Kujira; Naoki Suzuki; Tomoya Sakata, all if Inashiki, Japan

[73] Assignee: Mitsubishi Petrochemical Co., Ltd., Tokyo, Japan

[21] Appl. No.: 153,424

[22] Filed: Nov. 16, 1993

[30] Foreign Application Priority Data

Nov. 30, 1992 [JP] Japan ............................... 4-320588

[51] Int. Cl.$^6$ ............................................. C07C 51/21
[52] U.S. Cl. ..................................... 562/416; 562/412; 562/415
[58] Field of Search ......................................... 562/416

[56] References Cited

U.S. PATENT DOCUMENTS 3,256,324  6/1966  Landis et al. .

FOREIGN PATENT DOCUMENTS 464629  1/1992  European Pat. Off. .

Primary Examiner—José G. Dezs
Assistant Examiner—Dwayne C. Jones
Attorney, Agent, or Firm—Oblon, Spivak, McClelland, Maier & Neustadt

[57] ABSTRACT

A process for producing 2,6-naphthalenedicarboxylic acid by oxidizing 2,6-dimethylnaphthalene by molecular oxygen in the presence of a catalyst including cobalt, manganese and bromine. The oxidation reaction is performed by using a 2,6-dialkylnaphthalene mixture of 2,6-dimethynaphthalene and a small amount of 2,6-diisopropylnaphthalene as a raw material. Thus, the desired 2,6-naphthalenedicarboxylic acid can be produced at a high yield.

9 Claims, No Drawings

PROCESS FOR PRODUCING 2,6-NAPHTHALENEDICARBOXYLIC ACID

BACKGROUND OF THE INVENTION

1. FIELD OF THE INVENTION

The present invention relates to a process for producing 2,6-naphthalenedicarboxylic acid (hereinafter referred to as 2,6-NDCA). 2,6-NDCA is a useful compound serving as a raw material for highly functional resins such as polyethylene naphthalete (PEN resin), or the like.

2. DESCRIPTION OF THE RELATED ART

It is known that various processes are available for oxidizing 2,6-dimethylnaphthalene (hereinafter referred to as 2,6-DMN) by molecular oxygen in the presence of a catalyst including cobalt, manganese and bromine so as to produce 2,6-NDCA. For example, such processes are disclosed in Japanese Patent Laid-Open Nos. 48-34153 and 49-42564. However, they present the following problems. Unless a molar ratio of 2,6-DHN to acetic acid in the reaction system is maintained at a low level such as 1/100 or lower, intermediate oxidation products such as 6-formyl-2-naphthoic acid are increased, thus preventing high yields of 2,6-NDCA. Also, other processes are known such as a two-step oxidizing process where the temperature of the oxidation reaction is varried (Japanese Patent Publication No. 59-13495) and a process where the oxidizing is carried out in a solvent mixture of aliphatic carboxylic acid and an aromatic compound (Japanese Patent Laid-Open No. 64-3148). However, from the industrial point of view, the provision of a process for economically producing a high yield of 2,6-NDCA by using a small amount of a catalyst is desirable.

SUMMARY OF THE INVENTION

Accordingly, an object of the present invention is to provide a process for producing 2,6-NDCA from 2,6-DMN in the presence of an oxidizing catalyst including cobalt, manganese and bromine in which the yield of 2,6-NDCA can be improved without increasing cost or impairing production conditions.

In order to achieve the above objects, the present invention is to provide a process for producing 2,6-NDCA by oxidizing 2,6-DMN by molecular oxygen in the presence of a catalyst including cobalt, manganese and bromine, by using a 2,6-dialkylnaphthalene (hereinafter referred to as 2,6-DAN) mixture as raw material obtained by adding a small amount of 2,6-diisopropylnaphthalene (hereinafter referred to as 2,6-DIPN) as a minor raw material to 2,6-DMN as a major raw material.

DESCRIPTION OF THE PREFERRED EMBODIMENTS

Before citing Examples, the components, and various conditions and processes for the reaction in order to produce 2,6-NDCA will be discussed.

Raw material

The major raw material used in the present invention is 2,6-DMN. A small amount of 2,6-DIPN is added to 2,6-DMN so as to obtain the 2,6-DAN mixture. The molar ratio of 2,6-DMN to 2,6-DIPN is preferably between 99.99:0.01–90:10, and more preferably, between 99.9:0.1–95:5.

Any type of 2.6-DMN and 2.6-DIPN produced in any manner can be used.

Catalyst

Catalysts used for the present invention include cobalt, manganese and bromine. No particular limitations are imposed on cobalt compounds and manganese compounds used as catalyst components. Examples of cobalt and manganese compounds are aliphatic carboxylates such as formate, acetate, propionate, oxalate, and maleate of cobalt and manganese; alicyclic carboxylates such as naphthenate; aromatic carboxylates such as benzoate, terephtalate, naphthoate and naphthalenedicarboxylate; inorganic salts such as hydroxide, oxide, carbonate and halide. Among these components, acetate and bromide are particularly preferable.

A combination of a cobalt compound and a manganese compound is used for the reaction. The atomic ratio of the cobalt compound to the manganese compound is preferably between 99:1–1:99, and more preferably, between 95:5–5:95.

The total moles of cobalt and manganese atoms for use relative to 1 mole of 2,6-DAN is preferably between 0.0001–10 moles, and more preferably, between 0.001–5 moles.

As the bromine compound present in the catalyst components, inorganic bromine compounds, such as molecular bromine, hydrogen bromide, alkali metal bromide, alkaline earth metal bromide and hydrobromate; and organic bromine compounds, such as methyl bromide, ethyl bromide, bromoform, ethylene bromide and bromoacetic acid may be included. Among these compounds, potassium bromide is particularly preferable.

The number of moles of bromine atoms present in the bromine compound is between 0.1–10 times, and more preferably, between 0.2–5 times more than the total number of moles of cobalt and manganese atoms present in the solvent.

Solvent

As a solvent, aliphatic carboxylic acid, such as acetic acid, propionic acid and butyric acid may be used. A solvent mixture obtained by adding an Aromatic compound such as benzene or an aliphatic compound such as hexane to aliphatic carboxylic acid may be used. For using the solvent mixture, no particular conditions are specified as to the ratio of aliphatic carboxylic acid present in the solvent mixture. However, it is preferably 25% by weight or greater, and more preferably, 50% by weight or greater.

Also, although there are no particular conditions set for the amount of the solvent, it is preferably between 0.5–300 times by weight, and more preferably, between 1–150 times by weight greater than the amount of 2,6-DAN. There are no particular conditions set for the amount of water contained in the solvent.

Molecular oxygen

As molecular oxygen, although pure oxygen or pure oxygen diluted into a desired concentration with an inactivating gas such as nitrogen, helium, argon, or the like may be used, air will suffice.

Reaction conditions

The reaction temperature is preferably between 50°–300° C., and more preferably, between 70°–250° C. Temperatures outside these ranges are not preferable because a temperature lower than 50° C. considerably delays the reaction speed whereas a temperature higher than 300° C. causes an increase in losses due to combustion of the solvent or the component.

Although no particular conditions are set for the reaction pressure, if the reaction speed is taken into consideration, a reaction pressure such that the partial pressure of oxygen in the gas phase is at an absolute pressure of between 0.2-40 kg/cm$^2$ is desirable.

Reaction process

The reaction may be performed in a manner similar to a conventional liquid-phase oxidation process. For example, a batch process, a continuous process, or a combination of these two processes are available and any of these may be employed. The method for supplying 2,6-DAN to the reactor is not particularly defined and any of the following methods may be employed: charging the components of the 2,6-DAN mixture, a solvent and a catalyst together; continuously feeding 2,6-DAN to the reactor with which the solvent and the catalyst are already filled; feeding the homogeneously-mixed 2,6-DAN mixture; supplying 2,6-DAN and 2,6-DIPN to the reactor separately; and filling part of 2,6-DAN first and then, supplying the remaining 2,6-DAN to the reactor. 2,6-DAN may be melted or dissolved in a solvent for feeding.

Among these processes, it is preferable that the oxidation reaction be performed by the semi-batch reaction process.

The semi-batch reaction process is employed whereby although raw material is continuously supplied to the reaction system, the reaction product is not continuously taken out of the reaction system; instead, after the supply of raw material is stopped and the reaction is completed, the product is taken out. Thus, although this process differs from the batch reaction process and the continuous reaction process, it may be termed a combination of those two processes. The batch reaction process is employed whereby after raw material, a catalyst, and a solvent are charged in a reactor, the reaction is started, and after the reaction is completed, the product is taken out. The continuous reaction process is employed whereby the components are continuously supplied to the reactor and the product is continuously taken out. The semi-batch reaction process significantly improves the yield of 2,6-NDCA.

Such a semi-batch process allows to carry out the reaction while increasing the ratio of the catalyst amount to the amount of naphthalene derivatives remaining in the reaction liquid, thereby inhibiting the by-production of trimellitic acid. Furthermore, it also allows the selectivity of 2,6-DMN for 2,6-NDCA to be synergistically improved by adding a small amount of 2,6-DIPN.

The process for supplying 2,6-DAN to the reactor is not particularly defined as long as it is continuously supplied. For example, the following process is employed such that a catalyst and a solvent are charged in the reactor and the 2,6-DAN is fed while blowing a gas containing molecular oxygen. Alternatively, part of the 2,6-DAN (for example, up to 30% by weight, preferably less than 15% by weight) may be charged in the reactor together with a catalyst and a solvent with the remaining 2,6-DAN being continuously fed to the reactor, thus performing the oxidization reaction. The 2,6-DAN may be melted or dissolved into a solvent for feeding.

The 2,6-DAN should be fed so as to compensate for the loss due to the reaction. However, it is difficult to define the feeding speed generally since the optimal value varies depending on the conditions such as reaction temperature, pressure, and solvent amount. It is desirable to define the conditions so as to feed the whole amount of 2,6-DAN for 1-12 hours. Excessively high feeding speed lowers the catalyst concentration, thus increasing the possibility of a side reaction and by-products of trimellitic acid. If it takes more than 12 hours to feed the 2,6-DAN, the semi-batch process fails to achieve the practical effects of its use.

After-treatment of the product

After completing the reaction, the product is cooled to room temperature, and the crude 2,6-NDCA is separated by filtration and washed with a small amount of solvent. As a result, the solvent and most of the catalyst are recovered in the filtrate. Subsequently, the 2,6-NDCA is washed with water or dilute sulfuric acid, thereby removing impurities, such as a solvent and trimellitic acid, slightly present in the crude 2,6-NDCA so as to obtain highly purified 2,6-NDCA.

Examples will now be given in order to describe the present invention in more detail.

EXAMPLE 1

0.875g (5.60 mmol) of 2,6-DMN and 0.012 g (0.056 mmol) of 2,6-DIPN [5.66 mmol of the total 2,6-DAN], 44.5 mg (0.179 mmol) of cobalt acetate 4 hydrate, 11.0 mg (0.045 mmol) of manganese acetate 4 hydrate, 53.0 mg (0.448 mmol) of potassium bromide, and 20 ml of acetic acid were charged into an 100 cc autoclave. The pressure of the autoclave was raised by air to 100 kg/cm$^2$ at room temperature. The reaction system was heated and the temperature was then raised to 185° C. with the autoclave closed, and it was kept for 2 hours at a temperature of 185° C. under stirring. Subsequently, the autoclave was cooled to room temperature and the crude 2,6-NDCA was separated by filtration from the mixed reaction product. Then, 2,6-NDCA was washed with water containing 0.5% by weight sulfuric acid and the purity thereof was determined by liquid chromatography. Thus, 0.761 g (a yield of 62.4%) of 2,6-NDCA was obtained.

EXAMPLE 2

0.879 g (5.63 mmol) of 2,6-DMN and 0.006 g (0.03 mmol) of 2,6-DIPN [5.66 mmol of the total 2,6-DAN], 44.5 mg (0.179 mmol) of cobalt acetate 4 hydrate, 11.0 mg (0.045 mmol) of manganese acetate 4 hydrate, 53.0 mg (0.448 mmol) of potassium bromide, and 20 ml of acetic acid were charged into an 100 cc autoclave. An operation similar to Example 1 was performed. Thus, 0.759 g (a yield of 62.3%) of 2,6-NDCA was obtained.

COMPARATIVE EXAMPLE 1

0.884 g (5.66 mmol) of 2,6-DMN, 44.5 mg (0.179 mmol) of cobalt acetate 4 hydrate, 11.0 mg (0.045 mmol) of manganese acetate 4 hydrate, 53.0 mg (0.448 mmol) of potassium bromide, and 20 ml of acetic acid were charged into an 100 cc autoclave. An operation similar to Example 1 was performed. Thus, 0.68 g (a yield of 55.8%) of 2,6-NDCA was obtained.

COMPARATIVE EXAMPLE 2

1.20 g (5.66 mmol) of 2,6-DIPN, 44.5 mg (0.179 mmol) of cobalt acetate 4 hydrate, 11.0 mg (0.045 mmol) of manganese acetate 4 hydrate, 53.0 mg (0.448 mmol) of potassium bromide, and 20 ml of acetic acid were charged into an 100 cc autoclave. An operation similar to Example 1 was performed. Thus, 0.356 g (a yield of 29.1%) of 2,6-NDCA was obtained.

EXAMPLE 3

150 g of acetic acid, 0.125 g (0.5 mmol) of cobalt acetate 4 hydrate, 0.123 g (0.5 mmol) of manganese acetate 4 hydrate, 0.074 g (0.625 mmol) of potassium bromide were charged in a titanium-formed autoclave with 500 ml capacity equipped with a reflux cooling device, a gas-introducing pipe, a raw material feed pump, a back pressure regulator and a magnetic induction stirrer. The reaction system was replaced by nitrogen and the pressure of the reaction system was adjusted by the back pressure regulator so as to be 30 kg/cm$^2$G. The reaction system was heated until it was raised to a temperature of 200° C., and air and nitrogen were blown into the reaction system at 1.5 Nl/min and at 3.6 Nl/min. respectively so that the reaction system was adjusted to maintain an internal pressure of 30 kg/cm$^2$G. When the reaction system was stabilized, a mixture of 15.61 g (99.9 mmol) of 2,6-DMN, 0.021 g (0.1 mmol) of 2,6-DIPN and 200 g of acetic acid was continuously fed for 2.5 hours. A mixture of acetic acid and water was recovered through the condenser at a rate of approximately 80 g/hour. After completing the feeding of the components, the above gas mixture feeding was continued for 1 hour while maintaining the reaction system at a temperature of 200° C. and at 30 kg/cm$^2$G. After the reaction was over, the autoclave was cooled to room temperature and the precipitated solid was filtered so as to be recovered and washed with 40 g of acetic acid. After the obtained solid was washed with water by heat and further washed with purified water, it was dried. Thus, 19.79 g of 2,6-NDCA having a purity of 99.5% and a yield of 91.1% was obtained.

EXAMPLE 4

The reaction was performed under the same conditions as those of Example 3, except that a mixture of 0.125 g (0.5 mmol) of cobalt acetate 4 hydrate, 0.246 g (1.0 mmol) of manganese acetate 4 hydrate, 0.074 g (0.625 mmol) of potassium bromide was used as a catalyst-provided for the reaction and that a mixture of 15.59 g (99.8 mmol) of 2,6-DMN, 0.042 g (0.2 mmol) of 2,6-DIPN and 200 g of acetic acid was used as a feed component. The finally obtained solid was 19.95 g of 2,6-NDCA having a purity of 99.7% and a yield of 92.0%.

COMPARATIVE EXAMPLE 3

The reaction was performed under the same conditions as those of Example 1, except that a mixture of 15.62 g (100 mmol) of 2,6-DMN and 200 g of acetic acid was used as a feed component. The finally obtained solid was 19.05 g of NDCA having a purity of 99.8% and a yield of 87.9%.

What is claimed is:

1. A process for producing 2,6-naphthalenedicarboxylic acid by oxidizing 2,6-dimethylnaphthalene by molecular oxygen in the presence of a catalyst including cobalt, manganese and bromine; said process using a 2,6-dialkylnaphthalene mixture of 2,6-dimethynaphthalene and a small amount of 2,6-diisopropylnaphthalene as a raw material, thereby performing the oxidation reaction.

2. A process according to claim 1, wherein said 2,6-dialkylnaphthalene mixture essentially consists of 90-99.99 moles of 2,6-dimethynaphthalene and 0.01-10 moles of 2,6-diisopropylnaphthalene.

3. A process according to claim 2, wherein said 2,6-dialkylnaphthalene mixture essentially consists of 95-99.9 moles of 2,6-dimethynaphthalene and 0.1-5 moles of 2,6-diisopropylnaphthalene.

4. A process according to claim 1, wherein said oxidation reaction is performed at a temperature of between 50°-300° C.

5. A process according to claim 1, wherein said oxidation reaction is performed under pressure such that the partial pressure of oxygen in the gas phase is an absolute pressure of 0.2-40 kg/cm$^2$.

6. A process according to claim 1, wherein said oxidation reaction is performed in the presence of a solvent.

7. A process according to claim 6, wherein said solvent is one of an aliphatic carboxylic acid selected from the group consisting of acetic acid, propionic acid and butyric acid, and a solvent mixture of an organic solvent and 50% by weight or greater of said aliphatic carboxylic acid.

8. A process according to claim 1, wherein the amount of cobalt and manganese present in said catalyst is in a range of between 0.0001-10 moles as the total number of moles of cobalt and manganese atoms relative to 1 mole of 2,6-dialkylnaphthalene mixture.

9. A process according to claim 1, wherein the number of moles of atoms of a bromine compound present in said catalyst is in a range of between 0.1-10 times more than the total number of moles of cobalt and manganese atoms.

* * * * *

UNITED STATES PATENT AND TRADEMARK OFFICE
CERTIFICATE OF CORRECTION

PATENT NO.  : 5,442,103
DATED       : August 15, 1995
INVENTOR(S) : Hiroshi IWANE, et al.

It is certified that error appears in the above-indentified patent and that said Letters Patent is hereby corrected as shown below:

On the title page, Item [75], the inventorship should read:

--Hiroshi Iwane; Takahiro Sugawara; Katsufumi Kujira; Naoki Suzuki; Tomoya Sakata, all of Inashiki, Japan--

Signed and Sealed this

Twenty-first Day of November, 1995

*Attest:*

BRUCE LEHMAN

*Attesting Officer*     *Commissioner of Patents and Trademarks*